United States Patent [19]

Chaudhari et al.

[11] Patent Number: 5,498,801
[45] Date of Patent: Mar. 12, 1996

[54] PROCESS FOR THE CATALYTIC HYDROFORMYLATION OF ALKENES

[75] Inventors: Raghunath V. Chaudhari; Bhalchandra M. Bhanage; Sunil S. Divekar; Raj M. Deshpande, all of Maharashtra, India

[73] Assignee: Council of Scientific & Industrial Interest, New Delhi, India

[21] Appl. No.: 366,612

[22] Filed: Dec. 30, 1994

[51] Int. Cl.$^6$ .................................................. C07C 45/50
[52] U.S. Cl. ........................... 568/454; 568/429; 568/451
[58] Field of Search ........................... 568/451, 454, 568/429

[56] References Cited

U.S. PATENT DOCUMENTS

| | | | |
|---|---|---|---|
| 4,248,802 | 2/1981 | Kuntz | 568/454 |
| 4,778,905 | 10/1985 | Besson et al. | 556/16 |
| 5,223,648 | 6/1993 | Herrmann et al. | 568/429 |
| 5,289,918 | 2/1994 | Maher et al. | 568/454 |

OTHER PUBLICATIONS

Cornils "New Synthesis with Carbon Monoxide" edited J. Falbe, Spring Vallay, NY (1980).
Kalch et al "Adv. Organomet. Chem." vol. 34 pp. 219–284 (1992).
Renaud et al "J. Orgamet. Chem." vol. 419 p. 403 (1991).
Smith et al "Inorg. Chem. Acta." v 62 p. 135 (1982).

*Primary Examiner*—Werren B. Lone
*Attorney, Agent, or Firm*—Kenneth H. Johnson

[57] ABSTRACT

A process is effected using water soluble metal complex catalysts in the presence of a promoter in the organic (water immiscible) phase. The process results in the enhancement of the rate of hydroformylation by interfacial catalysis induced by the presence of a ligand (promoter) in a catalyst immiscible phase. The reaction comprises of two phases viz - organic phase and aqueous phase. The organic phase consists of an olefin and P- containing water insoluble ligand with or without water immiscible solvent. The aqueous phase consists of a metal complex catalyst comprising of group VIII element such as Rh, Ru, Ir or Co and a water soluble ligand.

20 Claims, No Drawings

PROCESS FOR THE CATALYTIC HYDROFORMYLATION OF ALKENES

The present invention relates to an improved process for the hydroformylation of internal and terminal alkenes. The process is useful particularly for the hydroformylation of alkenes having carbon atoms in the range of $C_2$–$C_{22}$. The process is effected using water soluble metal complex catalysts in the presence of a promoter in the organic (water immiscible) phase. The process results in the enhancement of the rate of hydroformylation by interfacial catalysis induced by the presence of a ligand (promoter) in a catalyst immiscible phase. The reaction comprises of two phases viz - organic phase and aqueous phase. The organic phase consists of an olefin and P- containing water insoluble ligand with or without water immiscible solvent. The aqueous phase consists of a metal complex catalyst comprising a group VIII element such as Rh, Ru, Ir or Co and a water soluble ligand of the type triphenylphosphine monosulfonate-sodium salt (TPPMS), triphenylphosphine disulfonate-sodium salt (TPPDS), triphenylphosphine trisulfonate-sodium salt (TPPTS), [2-(diphenyl phosphino) ethyl] trimethyl ammonium salt (amphos), [2-(diphenyl phosphino) ethyl] trimethyl phosphonium salt (phosphos) dissolved in water.

The aldehydes formed by hydroformylation have wide ranging applications in the perfumery industry and solvents besides being intermediates for solvents, plasticizers and detergent grade alcohols.

Hydroformylation reactions are industrially important for the manufacture of a wide range of compounds. The aldehydes ranging from $C_3$ to $C_{20}$ are synthesized using this process. These are further hydrogenated to oxo alcohols which find extensive applications as solvents and in the synthesis of plasticizers and detergents. The aldehydes particularly in the middle ($C_7$–$C_{12}$) range are also important in fragrance industries. Other miscellaneous applications of these products include lubricants, oil additives, metal extractive agents etc.

Hydroformylation reactions using homogeneous catalysts are well known in which the addition of carbon monoxide and hydrogen to an olefin in the presence of a metal complex catalyst soluble in the reaction medium, is involved.

The commercial oxo process based on Roelen's original work uses a homogeneous cobalt carbonyl complex catalyst $[CO_2(CO)_8]$ and is operated at 150 to 200 atm pressure, and 140°–180° C. temperature. High pressures of carbon monoxide are required to maintain the catalyst in active form since at lower carbon monoxide pressures, the catalytic complex decomposes to metallic cobalt. The side reactions occurring under these conditions are the hydrogenation of olefins, condensation of aldehydes, isomerization and formate formation.

A further modification of this process was a ligand modified cobalt process introduced by Shell Chemical Company. This process uses a hydridocobalt carbonyl trialkyl phosphine complex $[HCO(CO)_3(PBu_3)]$ and is operated at 50 atm and 200° C. temperature. This process is used to manufacture oxo alcohols directly, since this catalyst is also active for hydrogenation. Hydrogenation of olefins is a major side reaction in this process.

A Low Pressure Oxo Process based on a rhodium complex catalyst has been a major breakthrough in the oxo technology. The process utilizes a rhodium complex catalyst, hydrido rhodium carbonyl tris triphenylphosphine $[HRh(CO)(PPh_3)_3]$ and operates at 20 atm pressure and 100° C. temperature. A higher normal/branched aldehyde ratio is obtained and side reactions like hydrogenation and isomerization are negligible. This process is mainly used for the manufacture of butyraldehyde.

Use of this process for higher olefins has not been possible due to catalyst and product separation problems associated with the low volatility of higher aldehydes.

A significant development effected by Ruhrchemie and Rhone-Poulenc employs a water soluble rhodium complex catalyst. The reaction takes place in the aqueous phase containing the catalyst. The product aldehydes being immiscible with water, separate easily into the water immiscible phase. This process operates at reaction conditions comparable to the Low Pressure Oxo Process (Cornils B. in "New Synthesis with Carbon Monoxide" edited by J. Falbe, Springer Verlag, N.Y., 1980).

The synthesis of water soluble ligands has been instrumental in the development of biphasic hydroformylations using water soluble catalysis. A major breakthrough in this direction has been the synthesis of water soluble phosphine ligands [E. Kuntz U.S. Pat. No. 4,248,802 (1981)]. These water soluble phosphine ligands are synthesized by introducing a hydrophilic group on the ligands.

These phosphines generally occur in two major classes: (1) phosphines containing quarternized salt as the hydrophilic component e.g. (i) [2-(diphenyl phosphino) ethyl] trimethyl ammonium salt (amphos) (Smith & Baird in Inorg. Chem. Acta. 62, 135, 1982) (ii) [2-(diphenyl phosphino) ethyl] trimethyl phosphonium salt (phosphos) (Renaud et. al, in J. Organomet. chem. 419, 403 (1991)], and; (2) phosphines containing sulphonated groups as the hydrophilic component e.g. (i) triphenyl phosphine mono sulphonate sodium salt (TPPMS) and (ii) triphenyl phosphine trisulphonate sodium salt (TPPTS). Besides these major classes, other modifications of phosphines find limited applications (see Kalck and Monteil in Adv. Organomet. Chem 34, 219–284 (1992) and reference cited therein).

These ligands have been used for the formation of water soluble complexes of transition metals. Such complexes are used as hydroformylation catalysts in two phase (aqueous/organic) systems. The reaction system consists of an aqueous phase, comprising the metal complex along with the water soluble ligand. The organic phase consists of a reactant with or without water immiscible solvent cosolvent. The reaction occurs in the aqueous phase with dissolved reactants. The products (usually water insoluble) separate out into the organic phase thus making product separation and catalyst recycle/recovery easy.

The use of this process is, however, restricted to substrates having marginal solubility in water. Due to a very low solubility of most of the olefins in the aqueous catalytic phase, the rates of hydroformylation reaction using these catalysts are significantly lower than the conventional homogeneously catalyzed systems.

Use of $PPh_n(C_6H_4SO_3M)_{3-n}$ (M=alkali metal, alkaline earth metal/2, quaternary ammonium group); n=0, 1 or 2 and Rh or Rh compounds for hydroformylation of alkenes has been suggested in French Patent Fr 2,314,910 (1975). TPPTS and $[Rh(COD)Cl]_2$ were used at a pH of 7 to hydroformylate propene with 98% conversion to aldehydes and 87% selectivity to normal product.

A French Patent Fr 2,473,504 (1979) deals with hydroformylation of 1-hexene using cobalt catalysts and water soluble phosphines of the type TPPTS.

Propylene was hydroformylated using rhodium catalyst and waste soluble sulfonated phosphines to give corresponding aldehydes as reported in Fr 2,478,078 (1980).

In French Patent Fr 2,561,650 (1985) propene is hydroformylated using rhodium (II)-2-ethylhexanoate and TPPTS to give 100% selectivity to aldehyde and 93% to n-butanal.

For enhancing the solubility of a substrate by formation of a microemulsion, use of surfactant and cosurfactants has been suggested in a European Pat Appl. EP 380,154, (1990). A similar application has been described in a German patent DE 3,412,335 (1990) wherein surfactants like Me(CH$_2$)13N$^+$Me$_3$MeSO4— have been proposed to hydroformylate 1-hexene using rhodium catalyst and TPPTS to give 41% conversion. A reaction in the absence of a surfactant gave only 22% conversion for a similar period.

European Patent appl. EP 350,921 (1990) deals with hydroformylation of alkenes to alcohols and aldehydes in the presence of a water soluble catalyst containing cobalt complex with sulfonated water soluble phosphines.

Dinuclear rhodium complexes containing sulfonated triarylphosphines are also reported as hydroformylation catalyst in U.S. Pat. No. 4,778,905 (1985).

The hydroformylation catalysts described in the prior art using a biphasic system have a drawback of lower rates due to the solubility limitations of reactants in the aqueous phase. Although, the use of surfactant has been employed in the prior literature, there are problems associated with the separation of surfactants and products.

It is in this respect that the present invention provides an important process for the hydroformylation of olefins having a significant improvement employing the principle of interfacial catalysis by using a ligand in the water immiscible phase. This process leads to a dramatic increase in the rate of biphasic hydroformylation.

The main objective of the present invention is to improve the process for the hydroformylation of olefins particularly containing $C_{2-C22}$ carbon atoms. Another objective of the present invention is to promote an improved process for the hydroformylation of olefins so as to obtain higher rates of reaction. Another objective of the present invention is to apply this process for hydroformylations of internal or terminal and linear or branched olefins in biphasic media, using water soluble catalysts comprising group VIII metal complexes. Yet another objective of the present invention is also to cause the desired effect without using a co-solvent or surfactant. It was also the aim of this invention to get the said effect for hydroformylation of alkenes in the presence or absence of a solvent in organic phase. The process of the present invention involves promoting an interfacial catalytic reaction induced by addition of water insoluble ligands to the non-reacting organic phase.

The main findings underlying the present invention is as follows:

* It is observed that introduction of water insoluble ligand like tertiary aryl as well as alkyl phosphines and phosphites into the organic phase causes significant enhancement in reaction rate of a biphasic catalytic hydroformylation. The presence of a ligand in the organic phase having negligible solubility in the aqueous phase results in enriching the catalyst concentration substantially at the liquid-liquid interface and hence results in a dramatic enhancement in the rate of reaction.

The improved process as described in this invention has the following advantages over the processes described in the prior art:

* Significant enhancement (25–100 times) in the rate of reaction of a biphasic catalytic hydroformylation as a result of interfacial catalysis.

* Negligible or no loss of catalyst to organic phase by leaching.

* Effective in the absence or presence of aliphatic or aromatic solvents.

The present invention is concerned with the modification of the conventional catalytic system for biphasic hydroformylation reactions.

The reaction system comprises two phases, aqueous and organic (water immiscible). The organic phase comprises a substrate with or without solvent (water immiscible) and water insoluble ligand. The aqueous phase comprises a catalyst containing group VIIIA metals along with water soluble ligand dissolved in the aqueous phase. The reaction is carried out by contacting hydrogen and carbon monoxide with the alkene and the catalyst in the aqueous-organic dispersion.

Examples of alkenes which can be used are preferably in a range of $C_{2-C22}$ terminal or internal, linear or branched alkene such as ethylene, propylene, butene, isobutene, pentene, hexene, heptene, nonene, decene, dodcene, tridecene, tetradecene, and higher olefins up to $C_{22}$. Cyclic olefins like cyclohexene, cyclooctene, etc. can also be hydroformylated by the process of the invention.

Examples of solvents, immiscible in water, which may be used in the process of the invention include aliphatic and aromatic hydrocarbon solvents like hexane, heptane, octane, decane, benzene, toluene, o-, m-, p- xylene, cyclohexane, ethyl acetate, diethyl ether, etc. However, it is not a prerequisite to use a solvent in the process of the invention.

Examples of water insoluble ligands added in the organic phase in the process of the invention include P- containing ligands of the type triphenyl phosphine, triphenyl phosphite, tributyl phosphine, tributyl phosphite, triethyl phosphine, triaryl and trialkyl phosphine, trialkyl and triaryl phosphite and mixed phosphines i.e. alkyl-aryl-phosphines, diphosphines, N-containing compounds like tertiary, secondary or primary amines, heterocycles, quinolines, isoquinolines, substituted quinolines, pyridines.

The catalyst used in the process of the present invention consists essentially of water soluble metal complexes prepared from group VIIIA metals (eg. cobalt, rhodium, ruthenium and iridium) or complexes of the said elements or compounds containing group VIII elements (e.g. metal carbonates, halides, sulphates, hydroxides, chlorates).

Examples of water soluble ligands which can be employed in the process of the present invention can be of the type PPh$_n$(C$_6$H$_4$SO$_3$M)$_{3-n}$ (M=alkali metal, alkaline earth metal/2, quaternary ammonium group); n=0, 1 or 2. Water soluble phosphines containing quaternary ammonium group, e.g. amphos and phosphines containing phosphonium or acetate, hydroxyl groups.

The process can be carried out at a temperature in the range of 30°–180° C., preferably in the range of 80°–120° C. The hydrogen partial pressure used may be between 5–2000 psig, preferably between 100–600 psig. The hydrogen gas employed may be pure hydrogen as available commercially or may be contaminated with inert gases like nitrogen up to 10%. The partial pressure of carbon monoxide gas used may vary between 5–2000 psig, preferably between 100–600 psig. The carbon monoxide gas employed may be pure CO as available commercially or may be contaminated with inert or hydrogen, up to a total of 10%. The ratio of H$_2$:CO used for the purpose of the present invention can vary between 1:0.2 to 1:5, preferably between 1:0.8 to 1:1.5. The molar ratio of catalyst:substrate (alkene) may be between 1:5 to 1:8000 preferably between 1:20 to 1:1000. The molar ratio of group VIII elements (used as the catalyst) to the water soluble ligands employed can be between 0.5 to 100, preferably between 1 to 20. The ratio of group VIII elements (used as the catalyst) to the water insoluble ligand can be between 0.01 to 50 most preferably between 0.1 to 5. The agitation speed employed for the present invention can vary between 300 to 2000 rpm. The phase holdup ratio employed can vary between 0.1 to 10 (aqueous to total liquid volume).

No process is hitherto known having such a dramatic increase in the rate of a biphasic catalytic reaction by interfacial catalysis induced by a promoter present in the catalyst immiscible phase.

The principle of the present invention is not restricted to hydroformylation only but can also be extended for application to other similar biphasic catalytic reactions like hydrogenation, carbonylation, telomerization, metathesis, polymerisation, etc.

The process of the invention is described in detail in the examples given below that are presented by way of illustration only and should not be considered to limit the scope of the invention.

EXAMPLE 1

The following charge consisting of aqueous and organic phases was introduced in a 50 cc microclave equipped with a magnetic drive type agitation system and connected to a reserve of gas under pressure containing equimolar mixture of CO and $H_2$. The aqueous phase consisted of 0.049 g (0.1 mmol) of dirhodium dicyclooctadienyl dichloride $[Rh(C_8H_{12})Cl,]_2$, representing 0.0002 g atom of Rh, dissolved in deaerated water containing 1.0 g of the trisodium salt of tris(sulfophenyl) phosphine (TPPTS) (1.2 mmol), and diluted to 10 $cm^3$ with deaerated water. The TPPTS was used from a stock solution of 50% w/w concentration in deaerated water. The molar ratio of Rh:TPPTS was 1:6. The organic phase consisted of 1-octene 2 $cm^3$ (12.7 mmol) in 13 $cm^3$ toluene along with triphenylphosphine 13 mg (0.05 mmol). The molar ratio of Rh:P was 1:0.25. The contents were heated up to 100° C. and the reaction was carried out at total pressure of 600 psi (CO/$H_2$=1) and a stirring speed of 900 rpm. The reaction was carried out to completion. The reaction was over in 14 minutes. The activity (moles of product formed per grams Rh per second) of this reaction was found to be $3.08\times10^{-4}$ mol/s/g. The analysis of the organic phase showed conversion of 98.6% octene with selectivity of 99.0% towards nonanal and 2-methyl octanal mixture. In contrast the reaction carried out in the absence of triphenyl phosphine in the organic phase (other charge is same as above) showed 40% conversion of 1-octene after 480 minutes. The activity of this reaction was found to be $3.59\times10^{-6}$ mol/s/g, which is 85 times less than that in the presence of $PPh_3$ in the organic phase.

EXAMPLE 2

Reaction as described in Example 1 was carried out except that the organic phase contained only 1-octene 15 $cm^3$ (95.5 mmol) along with triphenylphosphine (TPP). This reaction was found to go to completion in 68 minutes. The activity of this reaction was found to be $4.77\times10^{-4}$ mol/s/g. Conversion of 1-octene was found to be 99.2% with 98.6% selectivity towards nonanal and 2-methyl octanal mixture. In comparison the reaction in the absence of TPP had only 5% conversion after 240 minutes of reaction. Activity of this reaction was found to be $3.19\times10^{-7}$ mol/s/g. Selectivity towards aldehyde namely nonanal and 2-methyl octanal mixture was found to be greater than 95%.

EXAMPLE 3

A charge similar to that given in Example 2 was taken except that the tri-t-butylphosphine was used instead of triphenylphosphine in the same ratio of metal to phosphine. The reaction was completed in 77 minutes with octene conversion of 98.7% and selectivity of 99.2% towards nonanal and 2-methyl octanal mixture. The activity of this reaction was found to be $4.30\times10^{-4}$ mol/s/g.

EXAMPLE 4

A charge similar to that given in Example 2 was taken except that tri-t-phenylphosphite was used instead of triphenylphosphine in the same ratio of metal to phosphine. The reaction was completed in 70 minutes with octene conversion of 99.2% and selectivity of 98.5% towards nonanal and 2-methyl octanal mixture. The activity of this reaction was found to be $4.53\times10^{-4}$ mol/s/g.

EXAMPLE 5

A charge similar to that given in Example 1 was taken except that TPPTS 2 mmol was used. The ratio of Rh:TPPTS was 1:10 in this case. At the end of 70 minutes the reaction showed 98.6% conversion and selectivity to nonanal and 2-methyl octanal mixture was 98.2%. The activity of this reaction was found to be $5.47\times10^{-4}$ mol/s/g.

EXAMPLE 6

A charge similar to that given in Example 1 was taken. The reaction was carried out at 90° C. instead of 100° C. At the end of 31 minutes the reaction showed 99% conversion and selectivity towards nonanal and 2-methyl octanal mixture was 99.2%. The activity of this reaction was found to be $1.36\times10^{-4}$ mol/s/g. In comparison the reaction in the absence of triphenyl phosphine went to 20% conversion and the end of 300 minutes under similar conditions. The activity of this reaction was $2.78\times10^{-6}$ mol/s/g.

EXAMPLE 7

A charge similar to that given in Example 1 was taken. The reaction was carried out at 450 psi CO pressure and 300 psi $H_2$ pressure. The reaction was completed in 13 minutes. The activity of this reaction was $3.24\times10^{-4}$ mol/s/g. The conversion of 98.5% and selectivity of 99.1% towards nonanal and 2-methyl octanal mixture was observed. In comparison reaction under similar conditions in the absence of TPP went only to 50% conversion at the end of 420 minutes. The activity of this reaction was found to be $4.96\times10^{-6}$ mol/s/g. The selectivity to nonanal and 2-methyl octanal mixture was 96.5%.

EXAMPLE 8

A reaction as described in Example 1 was carried out except that the organic phase contained 1-tetradecene instead of 1-octene, 2 $cm^3$ (7.9 mmol) along with triphenylphosphine (TPP). This reaction was found to go to completion in 19 minutes. The activity of this reaction was found to be $1.36\times10^{-4}$ mol/s/g. A conversion of 1-tetradecene was found to be 98.2% with 97.3% selectivity to pentadecanal and 2-methyl tetradecanal mixture. In comparison the reaction in the absence of TPP had only 3.5% conversion after 240 minutes of reaction with the activity of $3.72\times10^{-6}$ mol/s/g. Selectivity to pentadecanal and 2-methyl tetradecanal mixture was found to be greater than 95%.

The invention claimed is:

1. In the process for the hydroformylation of alkenes comprising reacting alkenes with carbon monoxide and hydrogen using water soluble catalyst in a biphasic media comprising water and an organic medium to produce aldehydes wherein the improvement comprises inducing an interfacial reaction by addition of water immiscible promoters in the organic phase giving significant enhancement in the rate of reaction as compared to the conventional biphasic catalysts.

2. The process of claim 1 wherein the water immiscible promoter is selected from the group consisting of

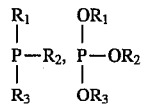

diphosphines, amines and nitrogen containing heterocyclics.

3. The process of claim 2 wherein said water immiscible promoter comprises a phosphorous containing water insoluble ligand.

4. The process of claim 3 wherein said phosphorous containing water insoluble ligand is selected from the group consisting of triaryl phosphines, trialkyl phosphines, trialkyl phosphites, triaryl phosphites and mixed phosphines.

5. The process of claim 1 wherein the alkene contain carbon atoms in the range of 2–22.

6. The process of claim 1 wherein the water soluble catalyst comprises a group VIII element.

7. The process of claim 6 wherein the water soluble catalyst comprises an element selected from the group consisting of Co, Ru, Rh and Ir.

8. The process of claim 6 containing a water soluble ligand selected from the group consisting of phosphines containing sulphonated groups, quaternary ammonium phosphine, quaternary phosphonium phosphine and mixtures thereof.

9. The process of claim 6 containing a water soluble ligand of the formula $PPh_n(C_6H_4SO_3M)_{3-n}$ wherein M=alkali metal, alkaline earth metal/2, quaternary ammonium group and n=0, 1 or 2.

10. The process of claim 1 wherein the temperature employed is in the range of 30° to 180° C.

11. The process of claim 10 wherein the temperature employed is in the range of 80° to 120° C.

12. The process of claim 1 wherein the hydrogen pressure employed is in the range of 5–2000 psi.

13. The process of claim 12 wherein the hydrogen pressure employed is in the range of 100–600 psi.

14. The process of claim 1 wherein the carbon monoxide pressure employed is in the range of 5–2000 ps.

15. The process of claim 1 wherein the carbon monoxide pressure employed is in the range of 100–600 psi.

16. The process of claim 1 wherein the ratio of carbon monoxide to hydrogen used is in the range of 1:0.2 to 1:5, preferably between 1:0.9 to 1:1.5.

17. The process of claim 1 wherein the ratio of carbon monoxide to hydrogen used is in the range of 1:0.9 to 1:1.5.

18. The process of claim 1 wherein the mole ratio of catalyst to substrate is in the range of 1:5 to 1:8000 mole.

19. The process of claim 1 wherein the mole ratio of catalyst to substrate is in the range of 1:20 to 1:1000 mole.

20. A process for the hydroformylation of alkenes using water soluble catalyst in a biphasic media comprising:
   a) forming an organo-water dispersion of
      i) an organic phase comprising (A) an alkene or an alkene and an organic solvent and (B) a water immiscible ligand and
      ii) an aqueous phase comprising a water soluble Group VIII metal catalyst composition and a water soluble ligand and ·
   b) contacting said dispersion with hydrogen and CO to provide an interfacial reaction between said alkene and said hydrogen and CO giving significant enhancement in the rate of reaction to produce aldehyde as compared to a reaction carried out in the absence of said water immiscible ligand.

* * * * *